United States Patent
Hsieh et al.

(10) Patent No.: US 10,206,448 B2
(45) Date of Patent: Feb. 19, 2019

(54) WEARABLE STEP-COUNTING SHOE

(71) Applicant: HOMEWAY TECHNOLOGY CO., LTD., Tainan (TW)

(72) Inventors: Chin-Hsing Hsieh, Tainan (TW); Tsung-Hsien Hsieh, Tainan (TW); Ming-Chia Hsieh, Tainan (TW); Tung-Chen Hsieh, Tainan (TW)

(73) Assignee: HOMEWAY TECHNOLOGY CO., LTD., Tainan (TW)

(*) Notice: Subject to any disclaimer, the term of this patent is extended or adjusted under 35 U.S.C. 154(b) by 65 days.

(21) Appl. No.: 15/402,668

(22) Filed: Jan. 10, 2017

(65) Prior Publication Data

US 2017/0325538 A1    Nov. 16, 2017

(30) Foreign Application Priority Data

May 10, 2016 (TW) .............................. 105206721 U

(51) Int. Cl.

| A43B 3/00 | (2006.01) |
|---|---|
| A43B 5/00 | (2006.01) |
| A43B 7/14 | (2006.01) |
| A43B 7/32 | (2006.01) |
| A63B 24/00 | (2006.01) |
| A63B 71/06 | (2006.01) |
| A43B 7/04 | (2006.01) |
| A43B 13/00 | (2006.01) |
| A61B 5/11 | (2006.01) |
| A61B 5/00 | (2006.01) |
| G01C 22/00 | (2006.01) |

(52) U.S. Cl.
CPC .............. *A43B 3/0005* (2013.01); *A43B 5/00* (2013.01); *A43B 7/04* (2013.01); *A43B 7/14* (2013.01); *A43B 7/32* (2013.01); *A43B 13/00* (2013.01); *A61B 5/1118* (2013.01); *A61B 5/6807* (2013.01); *A63B 24/0062* (2013.01); *A63B 71/0622* (2013.01); *G01C 22/006* (2013.01); *A61B 5/742* (2013.01); *A63B 2220/17* (2013.01); *A63B 2220/836* (2013.01)

(58) Field of Classification Search
CPC ............................ A43B 3/0005; A43B 3/0031
USPC ................................... 36/136, 137, 139, 132
See application file for complete search history.

(56) References Cited

U.S. PATENT DOCUMENTS 2,904,901 A * 9/1959 Goldstein ............ A43B 3/0031
36/1
4,402,147 A * 9/1983 Wu ...................... A43B 1/0054
235/105

(Continued)

*Primary Examiner* — Marie D Bays
(74) *Attorney, Agent, or Firm* — Muncy, Geissler, Olds & Lowe, P.C.

(57) ABSTRACT

A wearable step-counting shoe includes a shoe body and a pedometer. The shoe body includes a shoe sole having opposite inner and outer sides, and a groove surface defining amounting groove. The pedometer is removably disposed in the mounting groove and includes a pedometer body having opposite first and second faces and configured to detect and record the number of steps taken by a user, and a screen disposed on the second face and configured to display the detected number of steps. An engaging unit is provided to fix the pedometer on the shoe body, and includes a first engaging portion provided on the groove surface, and a second engaging portion provided on the pedometer and releasably engageable with the first engaging portion.

6 Claims, 4 Drawing Sheets

(56) References Cited

U.S. PATENT DOCUMENTS

| | | | | |
|---|---|---|---|---|
| 4,510,704 A * | 4/1985 | Johnson | ................... | A43B 3/00 |
| | | | | 235/105 |
| 4,891,797 A * | 1/1990 | Woodfalks | ............... | A43B 3/00 |
| | | | | 36/132 |
| 5,640,786 A * | 6/1997 | Buyayez | .................. | A43B 3/00 |
| | | | | 36/114 |
| 5,692,324 A * | 12/1997 | Goldston | ............. | A43B 1/0036 |
| | | | | 36/136 |
| 6,017,128 A * | 1/2000 | Goldston | ............. | A43B 1/0036 |
| | | | | 36/137 |
| 6,094,844 A * | 8/2000 | Potts | ................... | A43B 3/0031 |
| | | | | 36/136 |
| 8,028,443 B2 * | 10/2011 | Case, Jr. | .............. | A43B 1/0036 |
| | | | | 36/132 |
| 8,938,892 B2 * | 1/2015 | Case, Jr. | .............. | A43B 1/0036 |
| | | | | 36/132 |
| 2007/0169381 A1 * | 7/2007 | Gordon | ................... | A43B 3/00 |
| | | | | 36/132 |
| 2007/0247306 A1 * | 10/2007 | Case, Jr. | .............. | A43B 3/0005 |
| | | | | 340/539.11 |
| 2009/0284368 A1 * | 11/2009 | Case, Jr. | .............. | A43B 3/0005 |
| | | | | 340/539.1 |
| 2011/0314700 A1 * | 12/2011 | Case, Jr. | .............. | A43B 1/0036 |
| | | | | 36/132 |
| 2012/0293326 A1 * | 11/2012 | Case, Jr. | .............. | A43B 3/0005 |
| | | | | 340/539.13 |
| 2013/0247424 A1 * | 9/2013 | Tseng | ................... | A43B 3/0005 |
| | | | | 36/136 |
| 2016/0106177 A1 * | 4/2016 | De Laurentis | ..... | G08B 21/0286 |
| | | | | 340/539.13 |
| 2017/0258173 A1 * | 9/2017 | Johnson | ............... | A43B 3/0005 |

* cited by examiner

US 10,206,448 B2

WEARABLE STEP-COUNTING SHOE

CROSS-REFERENCE TO RELATED APPLICATION

This application claims priority of Taiwanese Patent Application No. 105206721, filed on May 10, 2016.

FIELD

This disclosure relates to a shoe, and more particularly to a wearable step-counting shoe having a step counting function.

BACKGROUND

People nowadays are more aware of how to keep themselves in good health by making constant exercises or movement and by maintaining a healthy positive life. To maintain a good posture and a good health is the goal of many people. Walking or brisk walking is an exercise that is moderate and suitable for men and women of all ages. In order to know whether the number of steps walked has reached a certain amount or not, some people will wear a pedometer on their bodies to record the number of steps. Recently, some industries have launched a shoe with a step-counting function (referred to as a step-counting shoe), so that when one wears the step-counting shoe, the number of steps can be detected and recorded. Thus, there is no need to wear a pedometer on his/her body.

Many sorts of designs of the step-counting shoe are available in the market. One of the conventional step-counting shoes has a step-counting function and a pedometer removably attached to the shoe. However, it does not have a screen for display. The step-counting result thereof must be sent to an external reader or processor. Thus, a user cannot right away know the step-counting information directly from his/her shoe. Use thereof is inconvenient.

SUMMARY

Therefore, an object of the present disclosure is to provide a wearable step-counting shoe that is capable of overcoming the aforesaid drawback of the prior art.

Accordingly, a wearable step-counting shoe of this disclosure includes a shoe body, a pedometer and an engaging unit. The shoe body includes a shoe sole having opposite inner and outer sides, and a groove surface extending from the inner side toward the outer side and defining amounting groove. The pedometer is removably disposed in the mounting groove and includes a pedometer body configured to detect the number of steps taken by a user, and a screen configured to display the detected number of steps. The pedometer body has a first face facing the shoe sole, and a second face opposite to the first face. The screen is disposed on the second face. The engaging unit is provided to fix the pedometer on the shoe body, and includes a first engaging portion provided on the groove surface of the shoe sole, and a second engaging portion provided on the pedometer and releasably engageable with the first engaging portion.

The efficiency of this disclosure resides in that the pedometer is provided with the screen which can directly display the step-counting result for viewing by a user to facilitate knowing the number of steps taken. The pedometer is removable to facilitate disposal and replacement thereof, so that use thereof is convenient. The engaging unit is provided to stably fix the pedometer on the shoe body.

BRIEF DESCRIPTION OF THE DRAWINGS

Other features and advantages of the disclosure will become apparent in the following detailed description of the embodiment with reference to the accompanying drawings, of which.

DETAILED DESCRIPTION

Figure 1:
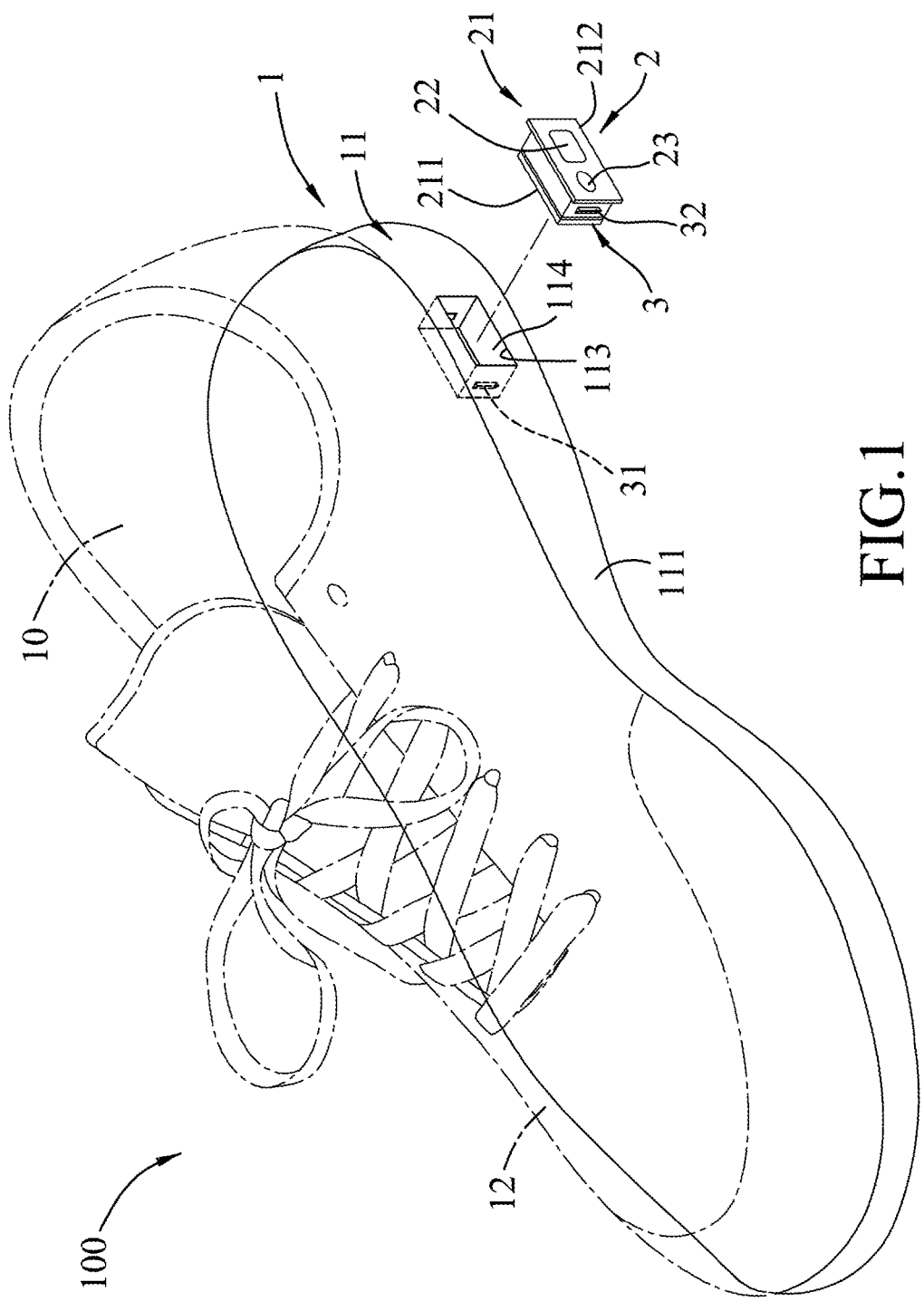
FIG. 1 is a perspective view of a wearable step-counting shoe according to the embodiment of the present disclosure with a shoe upper in phantom and with a pedometer being removed for the sake of clarity.
Figure 2:
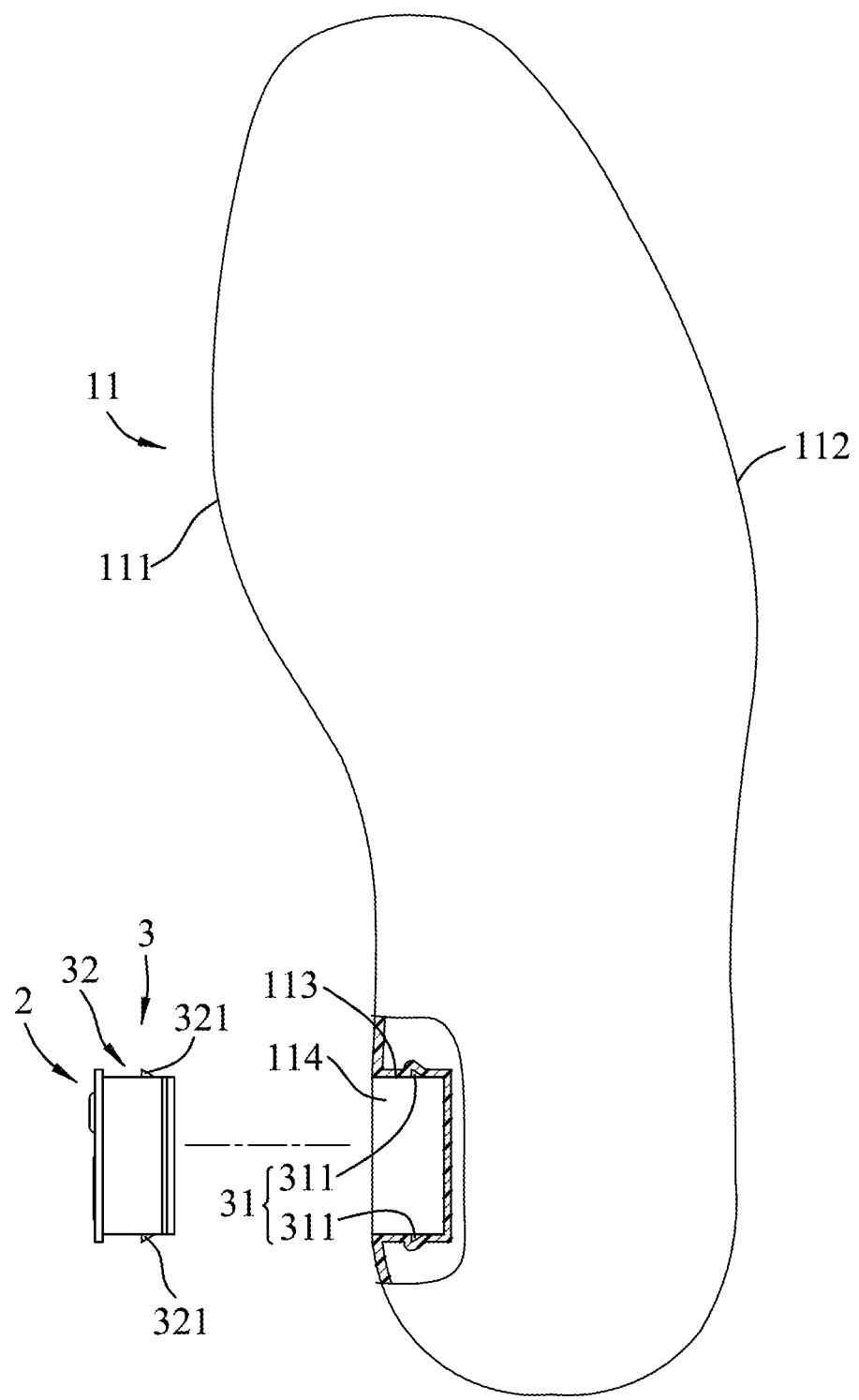
FIG. 2 is a schematic bottom view of FIG. 1.
Figure 3:
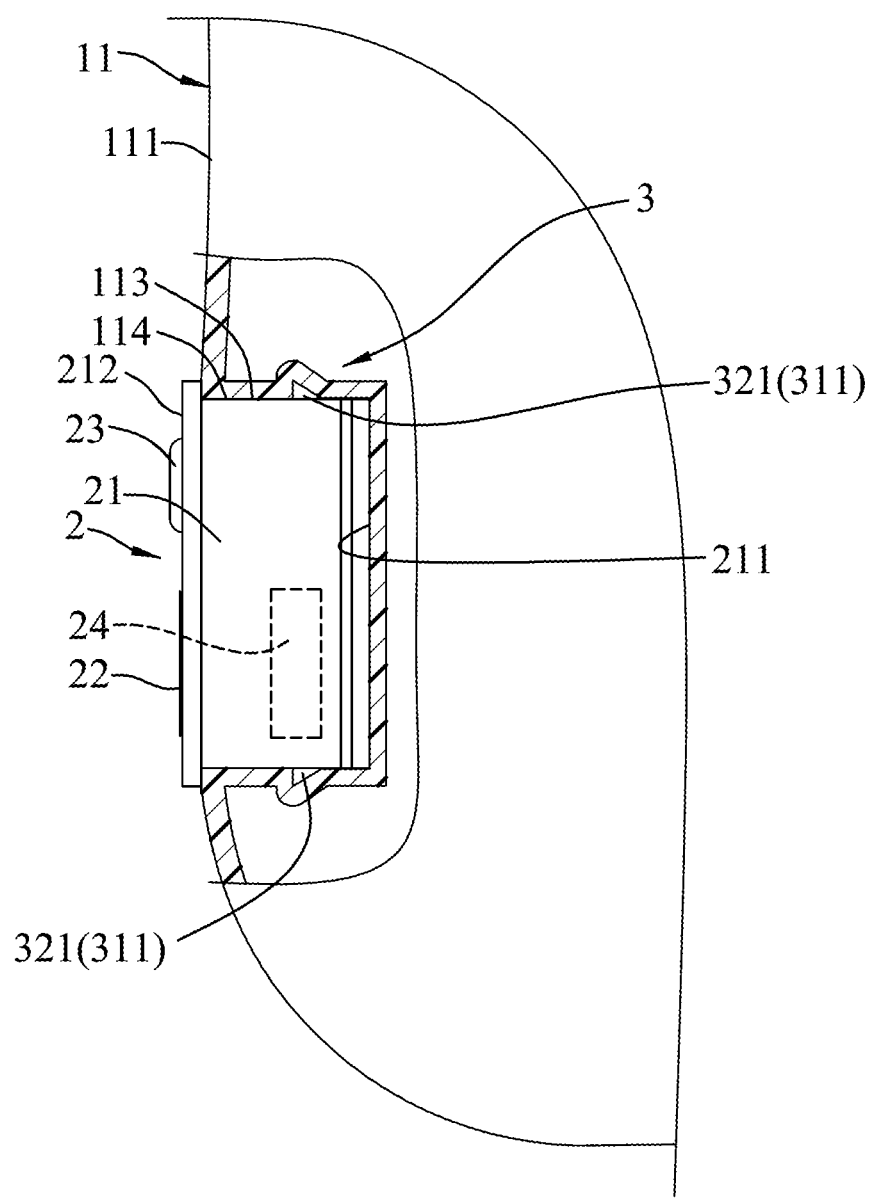
FIG. 3 is an enlarged fragmentary sectional view of the embodiment, illustrating how the pedometer is fixed to a shoe sole.
Figure 4:
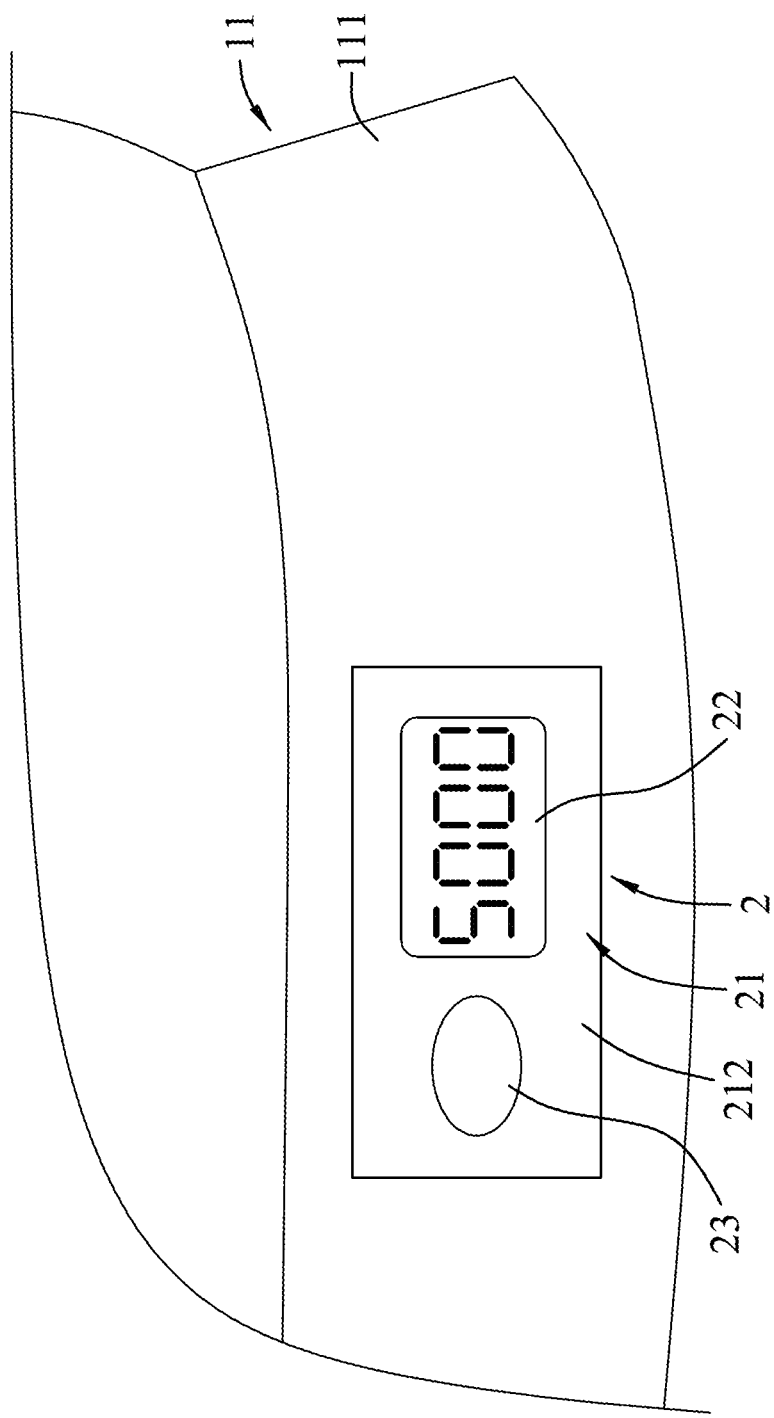
FIG. 4 is an enlarged fragmentary side view of the embodiment.

Referring to FIGS. 1 to 4, a wearable step-counting shoe 100 according to the embodiment of the present disclosure is exemplified as a shoe to be worn by the right foot of a user. In actual practice, the shoe 100 of this embodiment may also be a shoe for the user's left foot. The wearable step-counting shoe 100 includes a shoe body 1, a pedometer 2 and an engaging unit 3.

The shoe body 1 includes a shoe sole 11, and a shoe upper 12 connected to a top side of the shoe sole 11 and cooperating therewith to define a foot space 10. The shoe sole 11 is actually composed of a plurality of layers having elasticity and cushioning properties that are stacked up and down, and mainly includes a bottom sole contacting the ground, a midsole located above the bottom sole, and a liner located above the midsole for contacting the user's foot. Since the stack layered structure of the shoe sole 11 is not an important improvement of this disclosure, a detailed description thereof is omitted herein. The drawing also illustrates only a single layer of the shoe sole 11.

In this embodiment, the shoe sole 11 has opposite inner and outer sides 111, 112, and a groove surface 113 extending from the inner side 111 toward the outer side 112 and defining a mounting groove 114. The inner side 111 corresponds to an inner side of the user's foot. The outer side 112 corresponds to an outer side of the user's foot. The groove surface 113 is a continuous surface that completely separates the mounting groove 114 from other parts of the shoe sole 11, so that the mounting groove 114 will not communicate with the same. This can prevent rain water, water on the pavement or water from other sources from directly entering the other parts of the shoe sole 11 through the mounting groove 114. Hence, a good waterproof effect thereof can be achieved. Preferably, the shoe sole 11 is made of a heat-resistant material having excellent heat resistance that can alleviate abrasion of the shoe sole 11 caused by friction with the ground.

The pedometer 2 is disposed tightly and removably in the mounting groove 114, and includes a pedometer body 21 configured to detect and record the number of steps taken by the user, a screen 22, a reset button 23, and a battery 24 disposed in the pedometer body 21 for providing power. The pedometer body 21 has a first face 211 facing the shoe sole 11, and a second face 212 opposite to the first face 211. The screen 22, for example, an LCD display screen, is disposed on the second face 212, and is configured to display the detected number of steps taken by the user for viewing by the user. The reset button 23 is disposed side by side with the screen 22 on the second face 212, and is configured to reset the recorded number of steps to zero. Preferably, the reset button 23 is a silicone button which has a waterproof function. Moreover, the entire pedometer 2 can be designed to be waterproof.

The engaging unit 3 is provided to fix the pedometer 2 on the shoe body 1, and includes a first engaging portion 31 provided on the groove surface 113 of the shoe sole 11, and a second engaging portion 32 provided on the pedometer 2 and releasably engageable with the first engaging portion 31. In this embodiment, the first engaging portion 31 includes two recesses 311 formed oppositely in the groove surface 113 and communicating with the mounting groove 114. The second engaging portion 32 includes two protrusions 321 protruding outwardly and respectively from two opposite sides of the pedometer body 21. The protrusions 321 are releasably engageable with the respective recesses 311. In actual practice, the first engaging portion 31 may include one recess 311, and the second engaging portion 32 correspondingly includes one protrusion 321. The pedometer 2 may be similarly fixed on the shoe body 1. Thus, the number of the recess 311 and the protrusion 321 should not be limited to the disclosed embodiment. Further, the dispositions of the recess 311 and the protrusion 321 may be reversed. That is, the first engaging portion 31 may include a protrusion 321, while the second engaging portion 32 may include a recess 311.

During use of this disclosure, the user can raise his/her foot any time for viewing the number of steps detected and recorded by the pedometer 2. The position of the pedometer 2 is disposed on the inner side 111 of the shoe sole 11 through careful consideration. Thus, when the user raises his/her foot with the shoe 100 of this disclosure slightly and inwardly toward the other leg, he/she can then lower his/her head to directly view the number of steps displayed on the pedometer 2. Hence, use of this disclosure is quite convenient.

It is worth to mention herein that the pedometer 2 of this disclosure is designed to be removable, and has a simple structure and a low cost. When the pedometer 2 is out of power or damaged, the pedometer 2 can be removed from the shoe body 1 for disposal and replaced with a new one. To remove the pedometer 2, a flat end of a tool (not shown) may be used to extend between the pedometer 2 and the groove surface 113 so as to pull and remove the pedometer 2 from the mounting groove 114 and from the shoe body 1. Afterwards, a new pedometer 2 may be inserted into the mounting groove 114. This disclosure is provided with the mounting groove 114 for mounting of the pedometer 2 therein and being isolated from the other parts of the shoe sole 11, so that a good waterproof effect thereof can be achieved. The pedometer 2 is also waterproof. Even if the shoe 100 is worn on a rainy day or a pavement with accumulated water, the influence of water or moisture on the shoe 100 can be reduced. Furthermore, the shoe 100 of this disclosure has heat resistance and is crashproof, so that the service life thereof can be prolonged. When the wearable step-counting shoe 100 of this disclosure is worn by the user, he/she can fully grasp the number of steps of the daily walk or jogging to know the amount of daily exercise, so that a sports program can be easily planned to create a healthy life.

In sum, the shoe 100 of this disclosure can directly display the step-counting result for the user to view so that the user can readily and easily know the number of steps taken. The pedometer 2 is removable, so that when it is out of power or damaged, it can be removed and replaced with a new one, and there is no need to discard the entire shoe 100. Thus, the amount of garbage can be reduced, and the cost of replacing parts can be lowered. Use of this disclosure is very convenient. Furthermore, the pedometer 2 is light and small, so that after the shoe body 1 is mounted with the pedometer 2, the entire shoe 100 of this disclosure is lightweight, and is very easy to wear and walk. The design of the entire shoe 100 has waterproof, heat-resistant and crashproof functions, so that it is very practical to wear and is durable.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. A wearable step-counting shoe comprising:
   a shoe body including a shoe sole having opposite inner and outer sides, and a groove surface extending from said inner side toward said outer side and defining a mounting groove;
   a pedometer removably disposed in said mounting groove and including a pedometer body configured to detect and record the number of steps taken by a user, and a screen configured to display the detected number of steps, said pedometer body having a first face facing said shoe sole, and a second face opposite to said first face, said screen being disposed on said second face; and
   an engaging unit to fix said pedometer on said shoe body, said engaging unit including a first engaging portion provided on said groove surface of said shoe sole, and a second engaging portion provided on said pedometer and releasably engageable with said first engaging portions;
   wherein said first engaging portion includes a recess that is formed in said groove surface and that communicates with said mounting groove, and said second engaging portion includes a protrusion protruding outwardly from said pedometer body and releasably engageable with said recess.

2. The wearable step-counting shoe as claimed in claim 1, wherein said pedometer further includes a reset button disposed on said second face of said pedometer body and configured to reset the recorded number of steps to zero.

3. The wearable step-counting shoe as claimed in claim 2, wherein said reset button is a silicone button.

4. The wearable step-counting shoe as claimed in claim 1, wherein said groove surface completely separates said mounting groove from other parts of said shoe sole.

5. The wearable step-counting shoe as claimed in claim 1, comprising at least two separate first engaging portions and at least two separate second engaging portions.

6. The wearable step-counting shoe as claimed in claim 5, wherein said at least two second engaging portions are located on opposite sides of the pedometer body from each other.

* * * * *